United States Patent [19]

Renth et al.

[11] 4,146,638
[45] Mar. 27, 1979

[54] N-(3-PHENOXY-2-HYDROXY-PROPYL)-N-(2-PHENYL-2-HYDROXY-ETHYL)-AMINES

[75] Inventors: Ernst-Otto Renth, Ingelheim am Rhein; Anton Mentrup, Mainz-Kastel; Kurt Schromm, Ingelheim am Rhein; Herbert Köppe, Ingelheim am Rhein; Richard Reichl, Ingelheim am Rhein, all of Fed. Rep. of Germany

[73] Assignee: Boehringer Ingelheim GmbH, Ingelheim am Rhein, Fed. Rep. of Germany

[21] Appl. No.: 905,593

[22] Filed: May 15, 1978

Related U.S. Application Data

[63] Continuation-in-part of Ser. No. 768,487, Feb. 14, 1977, abandoned.

[30] Foreign Application Priority Data

Feb. 17, 1976 [DE] Fed. Rep. of Germany ....... 2606140

[51] Int. Cl.² .................. C07C 93/06; C07C 121/80; A61K 31/135; A61K 31/275
[52] U.S. Cl. ..................... 424/304; 562/451; 260/465 D; 260/465 E; 260/501.18; 260/556 A; 260/559 A; 260/562 A; 260/570.6; 560/42; 424/309; 424/316; 424/319; 424/321; 424/324; 424/330
[58] Field of Search ............ 260/465 D, 570.6, 559 A; 560/42; 424/304, 309, 324, 330

[56] References Cited

U.S. PATENT DOCUMENTS

| | | | |
|---|---|---|---|
| 3,278,601 | 10/1966 | Moed | 260/570.6 |
| 3,410,901 | 11/1968 | Kunz et al. | 260/570.6 |
| 3,892,799 | 7/1975 | Pinhas | 260/501.18 |
| 3,929,856 | 12/1975 | Holmes et al. | 260/465 E |
| 3,959,338 | 5/1976 | Koppe et al. | 260/465 E |

*Primary Examiner*—Dolph H. Torrence
*Attorney, Agent, or Firm*—Hammond & Littell

[57] ABSTRACT

Compounds of the formula

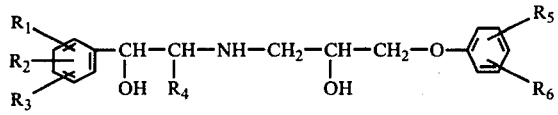

wherein
$R_1$ is halogen, hydroxyl, amino, alkyl, alkoxy or acylamido,
$R_2$ is hydrogen, hydroxyl, alkyl, alkoxy or carboxamido,
$R_3$ is hydrogen, halogen, alkyl or alkoxy,
$R_4$ is hydrogen, methyl or ethyl, and
$R_5$ and $R_6$ are each hydrogen, halogen, alkyl, alkoxy, benzyloxy, hydroxyl, amino, cyano, carboxyl, carbalkoxy, carboxamido, alkylenecarboxamido or acylamido, provided, however, that, when $R_1$ is 4-hydroxyl or 4-chloro, $R_2$ and $R_3$ are hydrogen, $R_4$ is methyl and $R_5$ is halogen or 2-halo, $R_6$ is other than 4-hydroxyl or 4-benzyloxy; and nontoxic, pharmacologically acceptable acid addition salts thereof. The compounds as well as their salts are useful as cardiotonics, vasodilators, hypotensives and antiarrhythmics.

6 Claims, No Drawings

N-(3-PHENOXY-2-HYDROXY-PROPYL)-N-(2-PHENYL-2-HYDROXY-ETHYL)-AMINES

This is a continuation-in-part of copending application Serial No. 768,487, filed February 14, 1977 and now abandoned.

This invention relates to novel N-(3-phenoxy-2-hydroxypropyl)-N-(2-phenyl-2-hydroxy-ethyl)-amines and non-toxic acid addition salts thereof, as well as to various methods of preparing these compounds.

More particularly, the present invention relates to a novel class of N-(3-phenoxy-2-hydroxy-propyl)-N-(2-phenyl-2-hydroxy-ethyl)-amines represented by the formula

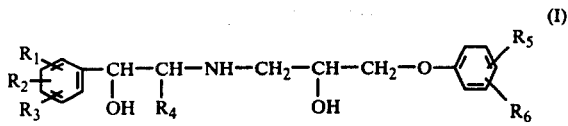

wherein
- $R_1$ is halogen, hydroxyl, amino, alkyl, alkoxy or acylamido,
- $R_2$ is hydrogen, hydroxyl, alkyl, alkoxy or carboxamido,
- $R_3$ is hydrogen, halogen, alkyl or alkoxy,
- $R_4$ is hydrogn, methyl or ethyl, and
- $R_5$ and $R_6$ are each hydrogen, halogen, alkyl, alkoxy, benzyloxy, hydroxyl, amino, cyano, carboxyl, carbalkoxy, carboxamido, alkylenecarboxamido or acylamido, provided, however, that, when $R_1$ is 4-hydroxyl or 4-chloro, $R_2$ and $R_3$ are hydrogen, $R_4$ is methyl and $R_5$ is halogen or 2-halo, $R_6$ is other than 4-hydroxyl or 4-benzyloxy; and non-toxic, pharmacologically acceptable acid addition salts thereof.

To the extent that above definitions of substituents $R_1$ to $R_6$ include alkyl or alkoxy or other groupings comprising alkyl or alkoxy radicals, these alkyl or alkoxy substituents and radicals are intended to mean those being straight or branched and having from 1 to 4 carbon atoms. The acyl moiety of the acylamido-substituents may be derived from lower aliphatic carboxylic acids or lower alkane-sulfonic acids, and the alkylene moiety of the alkylenecarboxamido-substituents is lower alkylene.

The following are preferred embodiments of the variable substituents in formula I:
- $R_1$ - Chlorine, bromine, hydroxyl, alkyl of 1 to 2 carbon atoms (primarily methyl), alkoxy of 1 to 2 carbon atoms (primarily methoxy), acetylamido, propionylamido and methanesulfonamido;
- $R_2$ - Hydrogen, hydroxyl, alkyl of 1 to 2 carbon atoms (primarily methyl) and alkoxy of 1 to 2 carbon atoms (primarily methoxy);
- $R_3$ - Hydrogen, chlorine, bromine, hydroxyl, alkyl of 1 to 2 carbon atoms (primarily methyl) and alkoxy of 1 to 2 carbon atoms (primarily methoxy);
- $R_4$ - Hydrogen and methyl;
- $R_5$ - Hydrogen, fluorine, chlorine, bromine, alkyl of 1 to 2 carbon atoms (primarily methyl), alkoxy of 1 to 2 carbon atoms (primarily methoxy), hydroxyl, cyano, carboxyl, carboxamido, benzyloxy, amino, carb(alkoxy of 1 to 2 carbon atoms), (alkylene of 1 to 2 carbon atoms)carboxamido and acylamido;
- $R_6$ - Hydrogen.

The compounds embraced by formula I may be prepared by the following methods which involve known chemical synthesis principles.

Method A

By removing one or more protective groups from a compound of the formula

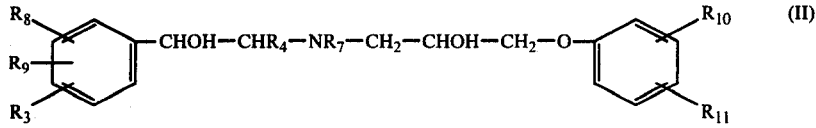

wherein $R_3$ and $R_4$ have the same meanings as in formula I, $R_7$ is hydrogen or arylmethyl,
- $R_8$ has the meanings defined for $R_1$ in formula I or is hydroxyl or amino protected by a protective group which can be removed by hydrogenation or hydrolysis,
- $R_9$ has the meanings defined for $R_2$ in formula I or is hydroxyl protected by a protective group which can be removed by hydrogenation or hydrolysis, and
- $R_{10}$ and $R_{11}$ have the meanings defined for $R_5$ and $R_6$, respectively, in formula I or are hydroxyl or amino groups protected by a protective group which can be removed by hydrogenation or hydrolysis, provided that at least one of $R_7$ through $R_{11}$ is a protected group of the type defined for each.

Examples of suitable protective groups are arylmethyl, alkanoyl, aroyl, tetrahydropyranyl and, for adjacent hydroxyls, bifunctional groups such as diarylmethylene. Specific examples of such protective groups are benzyl, substituted benzyl, lower aliphatic acyl, benzoyl and diphenylmethylene.

Arylmethyl protective groups attached to a nitrogen atom are removed by catalytic hydrogenation in the presence of conventional hydrogenation catalysts, such as platinum, palladium, Raney nickel or the like. Arylmethyl or diarylmethylene protective groups attached to an oxygen atom are removed by catalytic hydrogenation or by hydrolysis with acids. Alkanoyl, aroyl and tetrahydropyranyl protective groups are removed by hydrolysis.

If the starting compound contains substituents which the end product should also contain but which are likely to be altered under the conditions of the protective group removal reaction, sufficiently mild reaction conditions should be maintained so as not to alter these substituents. It is also possible, however, to start from a compound of the formula II wherein $R_{10}$ and $R_{11}$ are carbalkoxy or carboxamido, and simultaneously convert these during hydrolytic protective group removal into free carboxyl groups. The same applies analogously to the other preparative methods described herein.

The starting compounds of the formula II may be prepared by conventional methods, for instance by reacting an amine of the formula

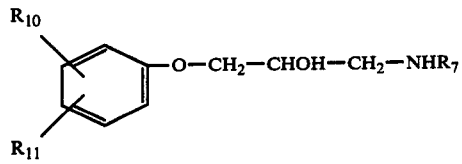 (III)

wherein $R_7$, $R_{10}$ and $R_{11}$ have the same meanings as in formula II, with a compound of the formula

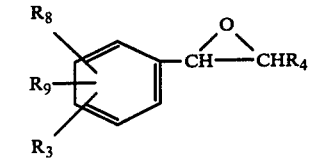 (IVa)

or

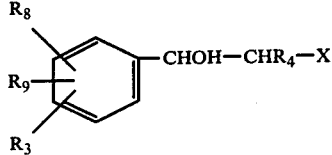 (IVb)

wherein $R_3$ and $R_4$ have the same meanings as in formula I, $R_8$ and $R_9$ have the same meanings as in formula II, and X is halogen, such as chlorine, in accordance with known methods.

The starting compounds of the formula II may also be obtained by method B described below, where, depending upon the particular reducing agent which is used, the erythro- or the threo-form is obtained.

Method B

By reducing the carbonyl group in a compound of the formula

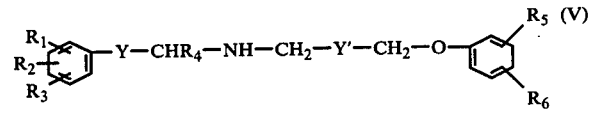 (V)

wherein $R_1$ through $R_6$ have the same meanings as in formula I, and one of Y and Y' is —CO— and the other is —CHOH—.

The reduction is carried out either (a) with a complex hydride, such as lithium aluminum hydride, sodium borohydride, potassium borohydride or sodium di-(2-methoxy-ethoxy) aluminum hydride (SDMA), or (b) with hydrogen in the presence of a hydrogenation catalyst, such as platinum, palladium or Raney nickel.

If the starting compound is one of the formula V wherein Y is carbonyl and $R_4$ is alkyl, the end product may be obtained either in the threo-form or in the erythro-form. Thus, if the reduction is carried out with a reducing agent mentioned under (a) above, the end product is a compound of the formula I in the threo-form. On the other hand, if it is carried out with the reducing agent mentioned under (b) above, the end product is a compound of the formula I in the erythro-form.

The starting compounds of the formula V may be obtained by known methods, for instance by reacting a compound of the formula

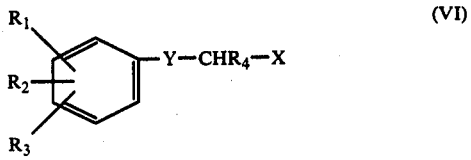 (VI)

wherein $R_1$ through $R_4$ have the same meanings as in formula I,

X is halogen, especially chlorine, and

Y has the meanings defined in formula V, with a compound of the formula

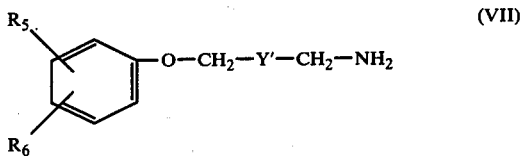 (VII)

wherein $R_5$ and $R_6$ have the same meanings as in formula I, and

Y' has the meanings defined in formula V.

Method C

By reacting an epoxide of the formula

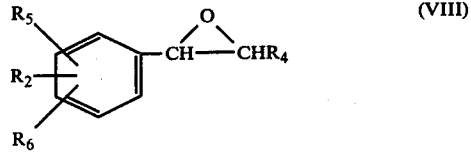 (VIII)

wherein $R_1$ through $R_4$ have the same meanings as in formula I, with a compound of the formula

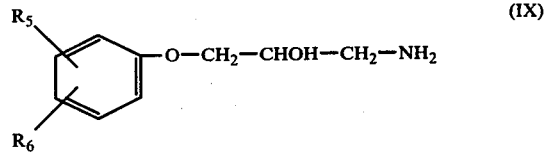 (IX)

wherein $R_5$ and $R_6$ have the same meanings as in formula I.

However, instead of starting with a compound of the formula VIII, it is also possible to start with a chlorohydrin of the formula

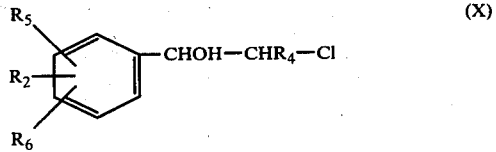 (X)

wherein $R_1$ through $R_4$ have the same meanings as in formula I, which converts into the corresponding epoxide of the formula VIII under the reaction conditions.

Method D

By reducing a Schiff's base of the formula

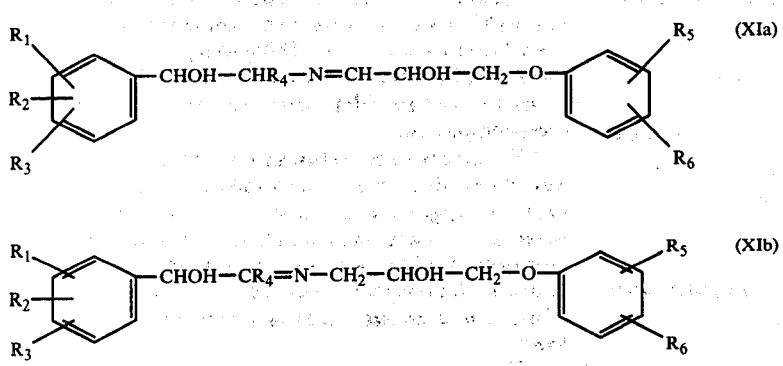

wherein $R_1$ through $R_6$ have the same meanings as in formula I, with hydrogen in the presence of a conventional hydrogenation catalyst or with a complex hydride.

Method E

By reducing an acid amide of the formula

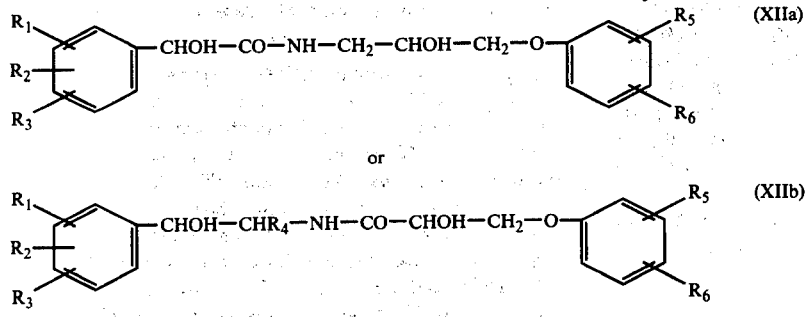

wherein $R_1$ through $R_6$ have the same meanings as in formula I, with a complex hydride, such a lithium aluminum hydride, SDMA or diborane.

Method F

By hydrolyzing an oxazolidinone or oxazolidine of the formula

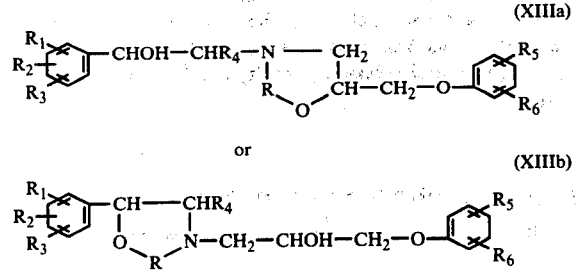

wherein $R_1$ through $R_6$ have the same meanings as in formula I, and

R is —CO— or —CHR'—, where R' is alkyl of 1 to 3 carbon atoms or aryl.

The hydrolysis is carried out in an alkaline medium or optionally in an acid medium; most advantageously it is performed at elevated temperatures in a mixture of water and a water-miscible solvent, such as methanol, ethanol or dioxane, in the presence of a base, preferably an alkali metal base.

This method is particularly well suited for the preparation of those end products of the formula I which do not contain phenolic OH-groups. It may also be used for the preparation of starting compounds of the formula II for method A which contain protective groups that are resistant to hydrolysis.

The oxazolidinone starting compounds of the formulas XIIIa and XIIIb may, for example, be prepared pursuant to the following reaction sequences:

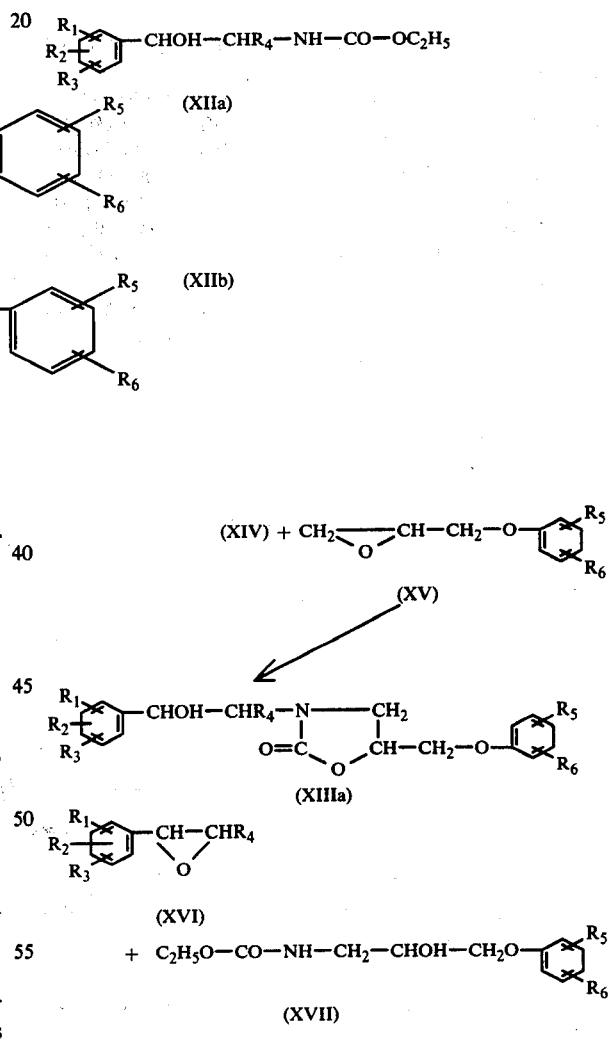

where $R_1$ through $R_6$ have the meanings previously defined.

Method G

By reacting an acetidinole of the formula

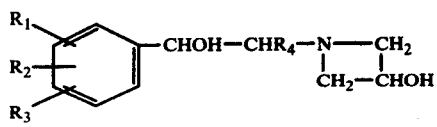

wherein $R_1$ through $R_4$ have the same meanings as in formula I, with a phenol of the formula

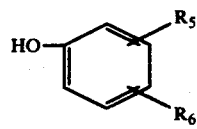

wherein $R_5$ and $R_6$ have the same meanings as in formula I.

The reaction is carried out at elevated temperatures, advantageously in an anhydrous, high-boiling-point solvent or solvent mixture, such as benzyl alcohol, in the presence of an alkali metal hydroxide, and preferably in an atmosphere of nitrogen. This method is generally suitable for the preparation of those compounds of the formula I which do not contain phenolic hydroxyl groups.

The starting compounds of the formula XVIII may be prepared by the following reaction sequence:

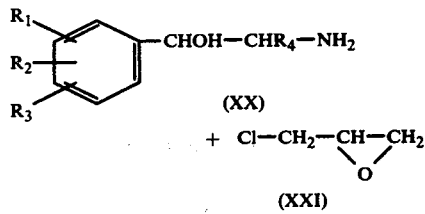

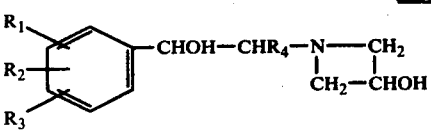

where $R_1$ through $R_4$ have the meanings previously defined.

The end products of the formula I and their salts exist as racemates, racemic mixtures and optionally active antipodes. If racemic starting materials are used to prepare them, the reaction products are in the racemic form; optically active starting materials yield optically active and products. Racemic end products may be separated into their optically active components by conventional methods.

If a separation into antipodes is contemplated, the R- or S-form of the starting compound of the formula V, for example, is used in method B; that is, a starting material with a uniform configuration in the —CHOH—group is used. Depending upon the starting material, the reduction of the carbonyl group then yields the RS- and RR-form or the SS- and SR-form of the end product.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, acetic acid, propionic acid, formic acid, fumaric acid, 8-chlorotheophylline or the like.

The following examples illustrate the present invention and will enable others skilled in the art to understand it more completely. It should be understood, however, that the invention is not limited to the particular examples given below.

EXAMPLE 1

1-[2-(p-Hydroxy-phenyl)-2-hydroxy-ethylamino]-3-(p-tolyloxy)-propanol-2 and its hydrochloride by method A 12 gm of α-aminomethyl-4-benzyloxy-benzyl alcohol and 9 gm of 2-(p-tolyloxy-methyl)-oxirane were dissolved in 60 ml of ethanol, and the solution was refluxed for 8 hours. Thereafter, the reaction solution was allowed to cool, was then suction-filtered, and the filter cake was dried. The compound thus obtained, 1-[2-(p-benzyloxy-phenyl)-2-hydroxy-ethylamino]-3-(p-tolyloxy)-propanol-2, was dissolved in 50 ml of methanol, palladized charcoal (10%) was added to the solution, and the intermediate was debenzylated by catalytic hydrogenation at room temperature and atmospheric pressure. After the calculated amount of hydrogen had been absorbed, the catalyst was separated by suction filtration, and the solvent was distilled off. The residue, 1-[2-(p-hydroxy-phenyl)-2-hydroxy-ethylamino]-3-(p-tolyloxy)-propanol-2, was dissolved in acetonitrile, and the calculated amount of ethereal hydrochloric acid was added to the solution. The substance which crystallized out was collected by suction filtration and dried, yielding the hydrochloride of the formula

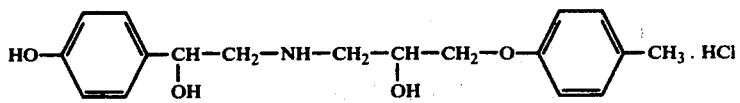

which had a melting point of 146° C.

EXAMPLE 2

1-[2-(p-Hydroxy-phenyl)-2-hydroxy-ethylamino]-3-(m-tolyloxy)-propanol-2 hydrochloride by method A (a) 15 gm of 4′-benzyloxy-2-bromo-acetophenone were dissolved in 150 ml of acetonitrile. While stirring, 13.5 gm of 1-benzylamino-3-(m-tolyloxy)-propanol-2 (m.p. 76°–77° C.) and 6.9 gm of anhydrous potassium carbonate were added. The resulting mixture was refluxed for 3 hours, then cooled and suction-filtered. The organic phase was admixed with the calculated quantity of ethereal hydrochloric acid. The hydrochloride of 4′-benzyloxy-N-benzyl-N-[2-hydroxy-3-(m-tolyloxy)-propyl]-2-amino-acetophenone (m.p. 147° C.) was allowed to crystallize out overnight, and was then collected by suction filtration and dried.

(b) 21 gm of the hydrochloric obtained in (a) were dissolved in water, the solution was admixed with ammonia until it was weakly alkaline, and then it was extracted with ether. The ether was evaporated from the extract solution in vacuo, the residue was dissolved in 200 ml of ethanol, and 1.5 gm of sodium borohydride were added. The mixture was made weakly acid with dilute acetic acid, the ethanol was distilled off in vacuo, the residue was dissolved in water, ammonia was added, and the alkaline aqueous solution was extracted with ether. The ether was distilled out of the extract in vacuo, the residue was taken up in acetonitrile, and the resulting solution was made acid with ethereal hydrochloric acid. The precipitate formed thereby was collected by suction filtration and dried, yielding the hydrochloride of 1-[2-(p-benzyloxy-phenyl)-2-hydroxy-ethyl-N-benzyl-amino]-3-(m-tolyloxy)-propanol-2, m.p. 128° C.

(c) For removal of the two protective benzyl groups, the hydrochloride obtained in (b) was dissolved in ten times its amount of methanol, palladized charcoal was added, and the mixture was hydrogenated under standard conditions until the calculated amount of hydrogen had been absorbed. Thereafter, the catalyst was separated by suction filtration, the filtrate was evaporated to dryness in vacuo, and the residue was dissolved in hot acetonitrile. The substance which crystallized out upon cooling was 1-[2-(p-hydroxy-phenyl)-2-hydroxy-ethylamino]-3-(m-tolyloxy)-propanol-2 hydrochloride, m.p. 149°-150° C.

EXAMPLE 3

1-[2-(m-Hydroxy-phenyl)-2-hydroxy-ethylamino]-3-(p-tolyloxy)-propanol-2-hydrochloride by method A A mixture consisting of 15.4 gm of 3'-benzyloxy-α-bromomethyl-benzyl alcohol, 13.5 gm of N-benzyl-2-hydroxy-3-(p-tolyloxy)-propylamine, 6.9 gm of anhydrous potassium carbonate and 100 ml of acetonitrile was refluxed for 5 hours. Thereafter, the reaction mixture was suction-filtered, and the filtrate was admixed with ethereal hydrochloric acid until it was weakly acid. The precipitate formed thereby was collected and, without further purification, immediately dissolved in methanol. Palladized charcoal was added to the solution, and the mixture was hydrogenated until the calculated amount of hydrogen had been absorbed. The catalyst was separated by suction filtration, the filtrate was evaporated to dryness in vacuo, the residue was dissolved in acetonitrile, and the solution was allowed to cool slowly. The following day the precipitate which had formed was collected by suction filtration and dried, yielding 1-[2-(m-hydroxy-phenyl)-2-hydroxy-ethylamino]-3-(p-tolyloxy)-propanol-2, m.p. 138°-140° C.

EXAMPLE 4

1-[2-(m-Hydroxy-phenyl)-2-hydroxy-ethylamino]-3-(o-cyano-phenoxy)-propanol-2 fumarate by method A (a) A mixture consisting of 11.3 gm of 2-(m-benzyloxy-phenyl)-ethyleneoxide (b.p. 152°-155° C. at 0.1 mm Hg), 16.8 gm of 1-benzylamino-3-(o-cyano-phenoxy)-propanol-2 (m.p. 181°-182° C.) and 50 ml of ethanol was refluxed for 8 hours. Thereafter, the ethanol was distilled off in vacuo, the residue was taken up in ethyl acetate, and ethereal hydrochloric acid was added to the weakly acid reaction. The acidic solution was allowed to stand overnight, and the precipitate was collected by suction filtration and dried, yielding the hydrochloride of 1-[2-(m-benzyloxy-phenyl)-2-hydroxy-N-benzyl-ethylamino]-3-(o-cyano-phenoxy)-propanol-2, m.p. 151°-152° C.

(b) The end product obtained in (a) was debenzylated by dissolving it in methanol, adding palladized charcoal to the solution, and hydrogenating it at room temperature, while shaking, until the calculated amount of hydrogen had been absorbed. Thereafter, the catalyst was removed by suction filtration, the filtrate was evaporated, the residue was dissolved in hot ethanol, and the calculated amount of fumaric acid was added to the solution. The mixture was allowed to cool slowly, and the precipitate which had formed was collected by suction filtration and dried, yielding the fumarate of 1-[2-(m-hydroxy-phenyl)-2-hydroxy-ethylamino]-3-[o-cyano-phenoxy]-propanol-2, m.p. 165°-167° C.

EXAMPLE 5

1-[2-(m,m'-dihydroxy-phenyl)-2-hydroxy-ethylamino]-3-(p-tolyloxy)-propanol-2-hydrochloride by method A 5.4 gm of p-cresol were dissolved in 50 ml of acetonitrile, and 13.8 gm of anhydrous potassium carbonate and 23.4 gm of 3,5-dibenzyloxy-α-N-(3-chloro-2-hydroxy-propyl)-aminomethyl-benzyl alcohol hydrochloride were added to the solution. The mixture was refluxed for 5 hours, then suction-filtered, and the filtrate was evaporated to dryness. The residue was dissolved in methanol and debenzylated by catalytic hydrogenation under standard conditions. The solution was then filtered, the methanol was distilled out of the filtrate, the residue was dissolved in hot acetonitrile, the calculated amount of ethereal hydrochloric acid was added to the hot solution, and the mixture was allowed to cool slowly. The crystalline precipitate formed thereby was collected by suction filtration and dried, yielding 1-[2-(m,m'-dihydroxy-phenyl)-2-hydroxy-ethylamino]-3-[p-tolyloxy]-propanol-2 hydrochloride, m.p. 169°-170° C.

EXAMPLE 6

1-[2-(p-hydroxy-phenyl)-2-hydroxy-ethylamino]-3-[o-methoxy-phenoxy]-propanol-2-sulfate by method A 19.9 gm of 1-amino-2-(o-methoxy-phenoxy)-propanol-2 and 28.6 gm of 4-benzyloxy-phenylglyoxal-hemiacetal (m.p. 77°-80° C.) were dissolved in 500 ml of methanol by heating to 40° C. The solution was allowed to stand overnight at room temperature. The next day, it was cooled to −10° C., and 7.4 gm of sodium borohydride were added in small portions. During this procedure and the subsequent 5 hours of reaction time, the temperature of the mixture was not allowed to rise above 0° C. It was then allowed to stand in the refrigerator overnight, and the precipitated crystals of 1-[2-(p-benzyloxy-phenyl)-2-hydroxy-ethylamino]-3-[o-methoxy-phenoxy]-propanol-2 were collected by suction filtration. The filter cake was dissolved in 20 times its amount of methanol, palladized charcoal was added, and the protective benzyl group was removed by catalytic hydrogenation. After removing the catalyst by suction filtration and distilling the methanol out of the filtrate in vacuo, the residue was dissolved in a little warm ethanol, and the calculated amount of concentrated sulfuric acid was added to the solution. The substance which crystallized out slowly was collected by suction filtration and dried, yielding the sulfate of 1-[2- hydroxy-phenyl)-2-hydroxy-ethylamino]-3-(o-methoxy-phenoxy)-propanol-2, m.p. 187°–188° C.

EXAMPLE 7

1-[2-(p-hydroxy-phenyl)-2-hydroxy-ethylamino]-3-(p-carboxamido-phenoxy)-propanol-2 hydrochloride by method A (a) A mixture consisting of 14.9 gm of 1-benzylamino-3-(p-carboxamido-phenyl)-propanone-2, 11.3 gm of (p-benzyloxy-phenyl)-ethyleneoxide and 100 ml of ethanol was refluxed for 8 hours. Thereafter, it was allowed to react overnight at room temperature, and then 2 gm of sodium borohydride were added. The mixture was stirred for 2 hours at room temperature and then for 2 hours at 70° C. Subsequently, the ethanol was distilled off in vacuo, the residue was admixed with water, and the aqueous mixture was acidified with acetic acid. Then it was made alkaline with ammonia and extracted several times with ethyl acetate. The solvent was distilled out of the combined extracts in vacuo, the residue was dissolved in boiling isopropanol and the solution was allowed to cool slowly. The precipitated crystals were collected by suction filtration and dried, yielding 1-[2-(p-benzyloxy-phenyl)-2-hydroxy-N-benzyl-ethylamino]-3-(p-carboxamido-phenoxy)-propanol-2, m.p. 111°–112° C.

(b) The end product obtained in (a) was dissolved in 10 times its amount of methanol, and after addition of palladized charcoal to the solution it was debenzylated by catalytic hydrogenation. After the calculated amount of hydrogen had been absorbed, the catalyst was removed by suction filtration, the solvent was distilled out of the filtrate in vacuo, the residue was dissolved in ethanol, and the solution was admixed with the calculated amount of ethereal hydrochloric acid. The substance which crystallized out was collected by suction filtration and dried in a drying chamber with forced air circulation; yielding the hydrochloride of the formula

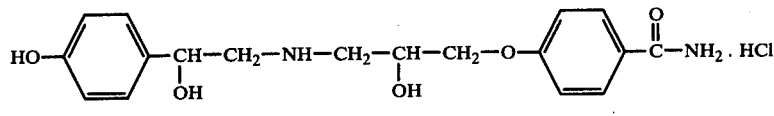

which had a melting point of 179°–180° C.

EXAMPLE 8

1-[2-(p-Hydroxy-phenyl)-2-hydroxy-ethylamino]-3-phenoxy-propanol-2-fumarate by method A 10.2 gm of 4-benzyloxy-N-[2-hydroxy-3-phenoxy)-propyl]-N-benzyl-mandelic acid amide were dissolved in 200 ml of absolute tetrahydrofuran. While stirring and simultaneously introducing nitrogen into the solution, 10 gm of lithium aluminum hydride were added, and the mixture was refluxed for 5 hours. Thereafter, it was cooled, and the excess lithium aluminum hydride was decomposed by slow addition of water. The liquid phase was decanted and evaporated to dryness. The residue was taken up in methanol, and after addition of palladized charcoal it was debenzylated by catalytic hydrogenation. After the calculated amount of hydrogen had been absorbed the catalyst was removed by suction filtration, the filtrate was evaporated in vacuo, the residue was taken up in a little ethanol, and a hot ethanolic solution of the calculated amount of fumaric acid was added. Upon cooling, the fumarate of 1-[2-(p-hydroxy-phenyl)-2-hydroxy-ethylamino]-3-phenoxy-propanol-2, m.p. 186° C., was obtained.

EXAMPLE 9

1-[2-(m,p-dichloro-phenyl)-2-hydroxy-ethylamino]-3-phenoxy-propanol-2 formate by method F A solution of 6 gm of 3-[2-(m,p-dichloro-phenyl)-2-hydroxy-ethylamino]-5-phenoxymethyl-oxazolidinone in 50 ml of ethanol was admixed with 10 gm of potassium hydroxide and 20 ml of water, and the mixture was refluxed for 90 minutes. After cooling, the ethanol was distilled off in vacuo. The aqueous residue was extracted twice with ether, and the combined ethereal extracts were washed with water and dried over magnesium sulfate. After distilling off the ether, the residue was dissolved in a little ethanol, formic acid was added to the solution, and then ether was slowly added. The formate crystallized out as a colorless substance.

Using procedures analogous to those described in the preceding examples and analogues starting compounds, the following compounds of the formula I and their salts were also prepared:

| Ex. No. | $R_1$ | $R_2$ | $R_3$ | $R_4$ | $R_5$ | $R_6$ | Salt* | m.p. [° C] |
|---|---|---|---|---|---|---|---|---|
| 10 | 4-OH | 3-OH | 2-CH$_3$ | H | 4-CH$_3$ | H | Cl | 244 (decomp.) |
| 11 | 4-OH | H | H | H | 3-CN | H | Cl | 154–156 |
| 12 | 4-OH | H | H | H | 2-CH$_3$ | H | FU | 123–125 |
| 13 | 4-OH | H | H | H | 2-CN | H | Cl | 135–136 |
| 14 | 4-OH | H | H | H | 4-CN | H | Cl | 157–159 |
| 15 | 3-OH | H | H | H | 2-CH$_3$ | H | FU | 122 |
| 16 | 3-OH | 5-OH | H | H | 4-CN | H | FU | 152–155 |
| 17 | 4-OH | H | H | H | 4-OCH$_3$ | H | Cl | 142–143 |
| 18 | 4-OH | H | H | H | 3-OCH$_3$ | 4-OCH$_3$ | Cl | 177–179 |
| 19 | 3-Cl | 4-Cl | H | H | H | H | FO | 189–190 |
| 20 | 4-OH | 3-NH$_2$ | H | H | 2-CH$_3$ | H | Cl | 210 (decomp.) |
| 21 | 4-OH | 3-NH—COCH$_3$ | H | H | 2-CH$_3$ | H | Cl | 158–159 |
| 22 | 4-OH | H | H | H | 4-CH$_2$—CONH$_2$ | H | FU | 171–172 |
| 23 | 4-OH | 3-OCH$_3$ | H | H | 4-CH$_3$ | 3-CH$_3$ | Cl | 148–149 |
| 24 | 4-OH | 3-CONH$_2$ | H | H | 4-CH$_3$ | H | Cl | 195–196 |
| 25 | 4-OH | H | H | CH$_3$(erythro) | 4-CN | H | Cl | 161–164 |
| 26 | 4-OH | H | H | CH$_3$(threo) | 4-CN | H | Cl | 169–171 |

*Cl = hydrochloride; FU = fumarate; FO = formate

The compounds of the present invention, that is, those embraced by formula I and their non-toxic, pharmacologically acceptable acid addition salts, have useful pharmacodynamic properties. More particularly, they exhibit cardiovascular, vasodilating, antihypertensive and anti-arrhythmic activities in warm-blooded animals, such as cats and dogs. Thus, for example, the compounds of this invention are useful as selective cardiotonics, since they produce a positive inotropic action with only a minor increase of the heart rate.

The selectivity is evidenced, for example, by tests on isolated guinea pig auricles. The following table shows the effects upon the amplitude and the frequency at a concentration of 1 μgm/ml of two representative species of this invention, where

| Compound | % change in Amplitude | Frequency |
|---|---|---|
| A | +37 | +7 |
| B | +36 | −3 |

A = 1-[2-(p-hydroxy-phenyl)-2-hydroxy-ethylamino]phenyl)-2-hydroxy-ethylamino]-3-(p-cyano-phenoxy)-propanol-2, and
B = 1-[2-(m,m'-Dihydroxy-phenyl)-2-hydroxy-ethylamino]-3-(p-tolyloxy-propanol-2.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.016 to 1.67 mgm/kg body weight, preferably 0.083 to 0.83 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise spcified.

| 1-[2-(p-Hydroxy-phenyl)-2-hydroxy-ethyl-amino]-3-(p-cyano-phenoxy)-propanol-2 | 5 parts |
|---|---|
| Stearic acid | 6 parts |
| Dextrose | 589 parts |
| Total | 600 parts |

Preparation:
The ingredients are admixed in conventional manner, and the composition is compressed into 600 mgm-tablets in a tablet making machine. Each tablet contains 5 mgm of the active ingredient and is an oral dosage unit composition.

EXAMPLE 28

Suppositories
The suppository composition is compounded from the following ingredients:

| 1-[2-(p-Hydroxy-phenyl)-2-hydroxy-ethyl-amino]-3-(p-tolyloxy)-propanol-2 hydrochloride | 50 parts |
|---|---|
| Lactose, powdered | 45 parts |
| Cocoa butter | 1605 parts |
| Total | 1700 parts |

Preparation:
The ingredients are admixed and the composition processed into 1700 mgm-suppositories in conventional manner. Each suppository contains 50 mgm of the active ingredient and is a rectal dosage unit composition.

EXAMPLE 29

Gelatin capsules
The capsule filler composition is compounded from the following ingredients:

| 1-[2-(m,m'-Dihydroxy-phenyl)-2-hydroxy-ethylamino]-3-(p-tolyloxy)-propanol-2 | 10 parts |
|---|---|
| Lactose | 490 parts |
| Corn starch | 500 parts |
| Total | 1000 parts |

Preparation:
The ingredients are admixed, the mixture is milled into a homogeneous powder, and 1000 mgm-portions of the powder are filled into hard gelatin capsules. Each capsule contains 10 mgm of the active ingredient and is an oral dosage unit composition.

Any one of the other compounds embraced by formula I or a non-toxic, pharmacologically acceptable acid addition salt thereof may be substituted for the particular active ingredient in Examples 27 through 29. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

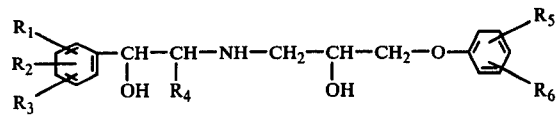

wherein
$R_1$ is halogen, hydroxyl, amino, alkyl of 1 to 4 carbon atoms, alkoxy of 1 to 4 carbon atoms, alkanoylamido of 1 to 5 carbon atoms or (alkane of 1 to 4 carbon atoms)sulfonamido, $R_2$ is hydrogen, hydroxyl, alkyl of 1 to 4 carbon atoms, alkoxy of 1 to 4 carbon atoms or carboxamido, $R_3$ is hydrogen, halogen, alkyl of 1 to 4 carbon atoms or alkoxy of 1 to 4 carbon atoms, —$R_4$ is hydrogen, methyl or ethyl, and $R_5$ and $R_6$ are each hydrogen, halogen, alkyl of 1 to 4 carbon atoms, alkoxy of 1 to 4 carbon atoms, benzyloxy, hydroxyl, amino, cyano, carboxyl, carbalkoxy of 1 to 5 carbon atoms, carboxamido, alkylenecarboxamido of 1 to 5 carbon atoms, alkanoylamido of 1 to 5 carbon atoms or (alkane of 1 to 4 carbon atoms)sulfonamido, provided, however, that, when $R_1$ is 4-hydroxyl or 4-chloro, $R_2$ and $R_3$ are hydrogen, $R_4$ is methyl and $R_5$ is halogen or 2-halo, $R_6$ is other than 4-hydroxyl or 4-benzyloxy; or a non-toxic, pharmacologically acceptable acid addition salt thereof.

2. A compound of claim 1,
where
$R_1$ is chlorine, bromine, hydroxyl, alkyl of 1 to 2 carbon atoms, alkoxy of 1 to 2 carbon atoms, acetylamido, propionylamido or methanesulfonamido;

$R_2$ is hydrogen, hydroxyl, alkyl of 1 to 2 carbon atoms or alkoxy of 1 to 2 carbon atoms;

$R_3$ is hydrogen, chlorine, bromine, hydroxyl, alkyl of 1 to 2 carbon atoms or alkoxy of 1 to 2 carbon atoms;

$R_4$ is hydrogen or methyl;

$R_5$ is hydrogen, fluorine, chlorine, bromine, alkyl of 1 to 2 carbon atoms, alkoxy of 1 to 2 carbon atoms, hydroxyl, cyano, carboxyl, carboxamido, benzyloxy, amino, carb(alkoxy of 1 to 2 carbon atoms), (alkylene of 1 to 2 carbon atoms)carboxamido or alkanoylamido of 1 to 3 carbon atoms; and $R_6$ is hydrogen.

3. A compound of claim 1, which is 1-[2-(p-hydroxyphenyl)-2-hydroxy-ethylamino]-3-(p-cyano-phenoxy)-propanol-2 or a non-toxic, pharmacologically acceptable acid addition salt thereof.

4. A compound of claim 1, which is 1-[2-(m,m'-dihydroxy-phenyl)-2-hydroxy-ethylamino]-3-(p-tolyloxy)-propanol-2 or a non-toxic, pharmacologically acceptable acid addition salt thereof.

5. A cardiotonic pharmaceutical dosage unit comosition consisting essentially of an inert pharmaceutical carrier and an effective cardiotonic amount of a compound of claim 1.

6. The method of selectively increasing the strength of contraction of the heart muscle of a warm-blooded animal, which comprises perorally or parenterally administering to said animal an effective cardiotonic amount of a compound of claim 1.

* * * * *

UNITED STATES PATENT OFFICE
CERTIFICATE OF CORRECTION

Patent No. 4,146,638  Dated March 27, 1979

Inventor(s) ERNST-OTTO RENTH; ANTON MENTRUP; KURT SCHROMM: HERBERT KOPPE and RICHARD REICHL It is certified that error appears in the above-identified patent and that said Letters Patent are hereby corrected as shown below:

Col. 1, line 9, "non-toxicacid" should read --non-toxic acid--.

Col. 4, line 33, "$R_5$" in formula VIII should read --$R_1$--.

Col. 4, line 39, "$R_6$" in formula VIII should read --$R_3$--.

Col. 4, line 57, "$R_5$" in formula X should read --$R_1$--.

Col. 4, line 63, "$R_6$" in formula X should read --$R_3$--.

Col. 9, line 3, "hydrochloric" should read --hydrochloride--.

Col. 11, line 1, "hydroxy-phenyl)" should read --(p-hydroxy-phenyl)--.

Col. 13, lines 22 and 23, "1-[2-(p-hydroxy-phenyl)-" should read --1-[2-(p-Hydroxy-phenyl)- --.

Delete "]phenyl)-2-hydroxy-ethylamino]"

Col. 13, line 24, after "tolyloxy" insert --)--.

UNITED STATES PATENT OFFICE
CERTIFICATE OF CORRECTION

Patent No. 4,146,638      Dated March 27, 1979

Inventor(s) ERNST-OTTO RENTH; ANTON MENTRUP: KURT SCHROMM: HERBERT KÖPPE and RICHARD REICHL It is certified that error appears in the above-identified patent and that said Letters Patent are hereby corrected as shown below:

Col. 13, between lines 45 and 46, the following should be inserted:

—EXAMPLE 27

Tablets:

The tablet composition is compounded from the following ingredients: —

Signed and Sealed this

Nineteenth Day of June 1979

[SEAL]

Attest:

RUTH C. MASON
Attesting Officer

DONALD W. BANNER
Commissioner of Patents and Trademarks